United States Patent [19]

Parsons

[11] Patent Number: 4,666,901

[45] Date of Patent: May 19, 1987

[54] SUBSTITUTED LACTAMS USEFUL AS ANGIOTENSIN CONVERTING ENZYME INHIBITORS

[75] Inventor: William H. Parsons, Rahway, N.J.

[73] Assignee: Merck & Co., Inc., Rahway, N.J.

[21] Appl. No.: 810,125

[22] Filed: Dec. 18, 1985

Related U.S. Application Data

[63] Continuation of Ser. No. 611,300, May 17, 1984, abandoned.

[51] Int. Cl.⁴ ..................... A61K 31/55; C07D 223/10
[52] U.S. Cl. .................................. 514/212; 540/463; 540/527
[58] Field of Search ................. 260/239.3 R; 514/212; 540/463, 527

[56] References Cited

U.S. PATENT DOCUMENTS 4,474,778 10/1984 Gordon et al. ..................... 540/527

Primary Examiner—Robert T. Bond
Attorney, Agent, or Firm—Salvatore C. Mitri; Michael C. Sudol, Jr.

[57] ABSTRACT

Substituted lactams and related compounds and methods for their preparation are disclosed. These compounds are useful as angiotensin converting enzyme inhibitors and as antihypertensives.

6 Claims, No Drawings

SUBSTITUTED LACTAMS USEFUL AS ANGIOTENSIN CONVERTING ENZYME INHIBITORS

This is a continuation of application Ser. No. 611,300, filed May 17, 1984, now abandoned.

BACKGROUND OF THE INVENTION

The invention is directed to substituted lactams having angiotension converting enzyme (ACE) inhibitor activity.

Lactams having ACE inhibitor activity are disclosed in European Patent applications EPO Nos. 46,291; 46,292; 46,289; and in U.S. Pat. Nos. 4,396,616 and 4,409,146.

A new class of N-substituted lactams having ACE inhibiting activity have been discovered.

SUMMARY OF THE INVENTION

The substituted lactam compounds of the invention have the general formula:

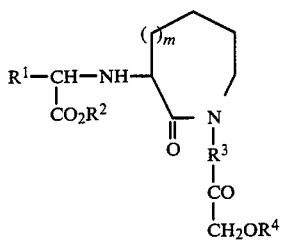

I wherein
m is 1 to 3;

$R^1$ is hydrogen; straight chain and branched $C_1-C_{12}$ alkyl; straight chain and branched $C_2-C_{12}$ alkenyl and alkynyl; $C_3-C_{10}$ cycloalkyl; substituted loweralkyl wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino, acylamino wherein the acyl group is derived from an organic acid; substituted loweralkylamino wherein the substituent can be halo, hydroxy, alkoxy or cyano; arloweralkylamino; cyclic amino; oxo, thio or ureido; aryloxy; arylthio; aralkyloxy; aralkylthio; benzofused cycloalkyl or bicycloalkyl of from 8-12 carbon atoms; aryl or heteroaryl which may be mono-, di- or trisubstituted by loweralkyl, hydroxy, loweralkoxy, halo, amino, acylamino, loweralkylthio or aminoloweralkyl; arloweralkyl; arloweralkenyl; heteroloweralkyl and heteroloweralkenyl in which the aryl or heteroaryl rings may be mono-, di- or tri-substituted by halo, loweralkyl, hydroxy, loweralkoxy, amino, loweralkylamino, diloweralkylamino, aminoloweralkyl, acylamino, carboxy, haloloweralkyl, nitro, cyano or sulfonamido; aralkyl or heteroaralkyl which include branched loweralkyl groups; substituted aralkyl or substituted heteroaralkyl which include branched loweralkyl groups wherein the loweralkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxy, hydroxyloweralkyl, trihaloloweralkyl, nitro, cyano, or sulfonamido; any of the arloweralkyl or aralkenyl and heteroloweralkyl or heteroloweralkenyl groups described above in which the aryl or heteroaryl ring is partially or completely hydrogenated; substituted loweralkyl having the formula $R_A{}^1(CH_2)_n—Q—(CH_2)_p$ wherein n is 0–2, p is 1–3, $R_A{}^1$ is aryl or heteroaryl optionally substituted by amino, lowerdialkylamino, loweralkylamino, hydroxy, hydroxyloweralkyl, aminoloweralkyl, trihaloloweralkyl, cyano, nitro sulfonamido, aroyl, loweralkyl, halo, dihalo, and loweralkoxy, and Q is O, S, SO, $SO_2$, $N—R_B{}^1$, $CONR_C{}^1$ $NR_C{}^1CO$, CH=CH wherein $R_B{}^1$ is hydrogen, loweralkyl, aryl, aralkyl, loweralkanoyl, or aroyl, and $R_C{}^1$ is hydrogen, or loweralkyl;

$R^2$ is hydrogen; loweralkyl; arloweralkyl or mono or disubstituted aryl wherein the substituents are halo, especially chloro;

$R^3$ is substituted or unsubstituted $C_1-C_3$ alkyl;

$R^4$ is H; loweralkanoyl; arloweralkanoyl; and,
the pharmaceutically acceptable salts thereof.

Pharmaceutically acceptable salts are salts of I with various inorganic and organic acids and bases. Such salts include ammonium salts, alkali metal salts e.g. sodium and potassium salts and the like, alkaline earth metal salts e.g. calcium and magnesium salts and the like, salts with organic bases, e.g. dicyclohexylamine salts, N-methyl-D-glucamine, salts with amino acids, e.g., arginine, lysine and the like, and salts with organic and inorganic acids, e.g., HCl, HBr, $H_2SO_4$, $H_3PO_4$, methanesulfonic, acetic, isethionic, toluenesulfonic, maleic, fumaric, camphorsulfonic, oxalic acids and the like.

The salts may be formed by conventional means, e.g. by reacting the free acid or free base form of the formula I with one or more equivalents of an appropriate base or acid in a suitable solvent or other reaction medium.

The alkyl substituents recited above denote straight and branched chain hydrocarbons of $C_1-C_{12}$ such as methyl, hexyl propyl, dodecyl isopentyl, isopropyl, nopentyl, etc.

Loweralkyl denotes alkyl groups of $C_1$ to $C_8$ such as ethyl, isobutyl, 4-methylpentyl, and the like.

Alkenyl and alkynyl denote alkyl groups as described above which are modified so that each contains a carbon to carbon double bond or triple bond, respectively, such as vinyl, 2-butenyl and 1-hexynyl.

Cycloalkyl denotes rings composed of 3 to 10 methylene groups, each which may be substituted or unsubstituted with other hydrocarbon substituents, and include, for example, cyclopentyl, cycloheptyl, 4-methyl cyclohexyl, and the like.

Benzofused cycloalkyl groups denote a cycloalkyl ring of 5 to 8 carbon atoms to which is fused a benzene ring such as indanyl or tetralyl groups.

Bicycloalkyl denotes two cycloalkyl rings of 5 to 8 carbon atoms each joined together in any allowable way such as perhydroindane, octahydronaphthalene, bicyclo 3:1:3 octane and spiro 4:0:4 nonane.

The loweralkoxy substituent represents loweralkyl groups as described above attached through an oxygen bridge.

The aralkyl and heteroaralkyl substituents recited above represent aryl or heteroaryl groups as herein defined attached through a straight or branched chain hydrocarbon of from one to six carbon atoms, for example, benzyl, phenethyl, 3,3-diphenylpropyl, 3-indolylmethyl, and the like.

Halo means chloro, bromo, iodo, or fluoro.

The aryl substituent represents phenyl, naphthyl, or biphenyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl; as well as any bicyclic group in which any of the above heterocyclic rings is fused to another aromatic ring, for example, indolyl, quinolinyl, isoquinolinyl, benzimidazolyl, benzothiazolyl, benzthienyl, and naphthyridyl.

The acylamino substituent is derived from an organic acid carboxyl group and represents loweralkanoylamino and aroylamino.

Preferred are those compounds of Formula I wherein:

m is 1 or 2;

$R^1$ is alkyl having from 1 to 8 carbon atoms; substituted lower alkyl wherein the alkyl group has 1–5 carbon atoms and the substituent is amino, acylamino, hydroxy, aminoloweralkylthio, aminoloweralkoxy, arylthio, aryloxy or arylamino, aralkyl or heteroaralkyl wherein the alkyl portion has 1 to 3 carbon atoms (such as phenethyl or indolylethyl) or substituted arloweralkyl (phenyl lower alkyl or naphthyl lower alkyl) and substituted heteroarloweralkyl wherein the alkyl groups have 1–3 carbons optionally substituted with amino, hydroxy or acylamino and wherein the substituent(s) on the aryl or heteroaryl groups is halo, dihalo, amino, aminoalkyl, hydroxy, lower alkoxy, lower alkyl, phenoxy or benzoyl;

$R^2$ is hydrogen; loweralkyl; arloweralkyl;

$R^3$ is $(CH_2)_q$ where q is 1 or 2; and, $R^4$ is hydrogen.

More preferred are compounds of Formula I wherein m is 1 or 2;

$R^1$ is alkyl from 1 to 8 carbon atoms; substituted lower alkyl wherein the alkyl group has 1–5 carbon atoms and the substituent is amino, acylamino, hydroxy, aminoloweralkylthio, arylthio, aryloxy; aralkyl or heteroaralkyl wherein the alkyl portion has 1–3 carbon atoms (such as phenethyl or indolylethyl) or substituted arloweralkyl and substituted heteroarloweralkyl wherein the alkyl groups have 1–3 carbons optionally substituted with amino, hydroxy or acylamino and wherein the substituent(s) on the aryl or heteroaryl groups is halo, amino, aminoalkyl, hydroxy, or lower alkoxy;

$R^2$ is hydrogen; loweralkyl; arloweralkyl;

$R^3$ is $(CH_2)_q$ where q is 1 or 2; and $R^4$ is hydrogen.

Most preferred are compounds of Formula I wherein m is 1 or 2;

$R^1$ is alkyl of 1–8 carbons; substituted lower alkyl wherein the alkyl group has 1–5 carbon atoms and the substituent is amino, acylamino, hydroxy, arylthio, aryloxy; aralkyl or heteroaralkyl wherein the alkyl portion has 1–3 carbon atoms (such as phenethyl or indolylethyl); substituted arloweralkyl or substituted heteroarloweralkyl wherein the alkyl groups have 1–3 carbons and the substituents in the aryl or heteroaryl groups are halo, amino, aminoalkyl, hydroxy, or lower alkoxy;

$R^2$ is hydrogen; loweralkyl; benzyl;

$R^3$ is $(CH_2)_q$ where q is 1 or 2; and $R^4$ is hydrogen.

Especially preferred are compounds of Formula I wherein $R^1$ is

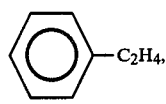

$R^2$ and $R^4$ are independently selected from H and lower alkyl, preferably ethyl, m is 1 or 2, preferably 1, and $R^3$ is $(CH_2)_2$— or $(CH_2)_3$, preferably $(CH_2)_2$.

In the compounds of Formula I, the carbon atom to which $R^1$ is attached, the ring carbon atom to which the fragment

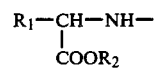

is attached, and the $R^3$ group when appropriately substituted, may be chiral centers. Thus, the compounds of this invention exist in and include all diastereoisomeric forms or mixtures thereof. The mixtures may be resolved if desired by crystallization of salts of optically active acids or bases or by other methods known in the art. These part-structures

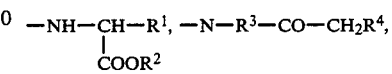

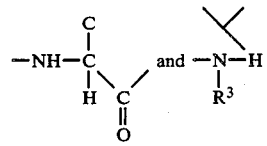

of Formula I can be in two configurations (S or R) and both are within the scope of this invention, although S is generally preferred.

The compounds of Formula I may be prepared by any convenient process.

One such process is illustrated by the following set of equations:

Process 1

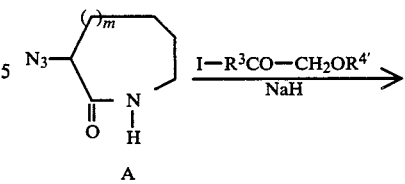

A

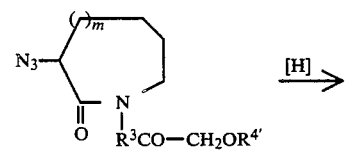

B

-continued
Process 1

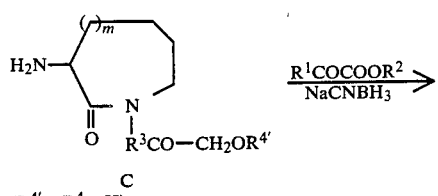

C
($R^{4'}=R^4=H$)

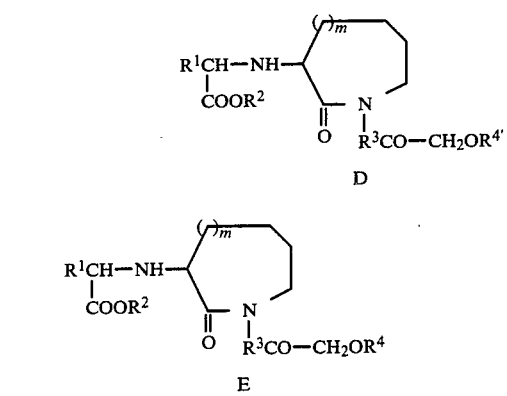

The conversion of C to D is a reductive coupling and is carried out in a reducing system such as ethanol/Pd on C or using a reducing agent such as $NaCNBH_3$. Conversion of D to E ($R^4=H$) may be carried out by hydrolysis (acidic or basic or by hydrogenoysis depending on the desired structures of $R^2$ and $R^4$ in I.

A general process for preparing A and B is described in European Patent Application No. 46,289 and is illustrated by the following equations for the system in which $m=2$.

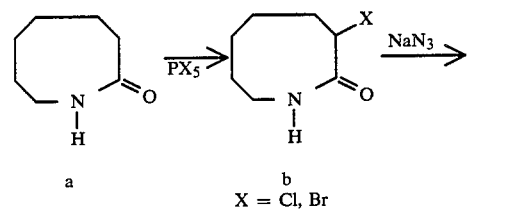

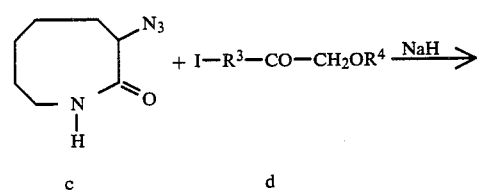

Perhydroazocin-2-one (a) or an 8-substituted derivative prepared from a 2-substituted cycloheptanone by the procedure of Blicke et al., [*J. Am. Chem. Soc.*, 76, 2317 (1954)] is converted to (b), with $PX_5$, X=Br or Cl [Nagasawa et al., *J. Med. Chem.*, 14, 501 (1971)]. Reaction of (b) with sodium or lithium azide in a suitable solvent such as DMF or ethanol [see, for example, Brenner et al., *Helv. Chem. Acta.* 41, 181 (1958)] affords (c) which can be alkylated with an iodoester (d) in the presence of a strong base, like sodium hydride, in a solvent such as dimethylformamide (DMF) or tetrahydrofuran (THF) to produce (e).

Alternatively, (b) may be alkylated with (d) in the presence of a strong base, like sodium hydride, and the intermediate (f) converted to (e) by reaction with an azide salt as illustrated by the following equations:

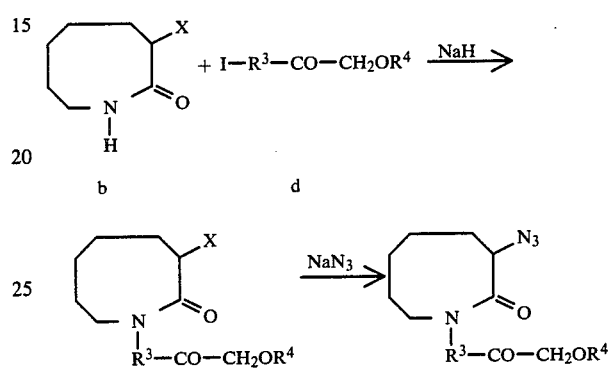

These processes may also be applied in the 7($m=1$) and 9($m=3$) membered lactam series.

Another useful process is illustrated by the following equation:

Process 2

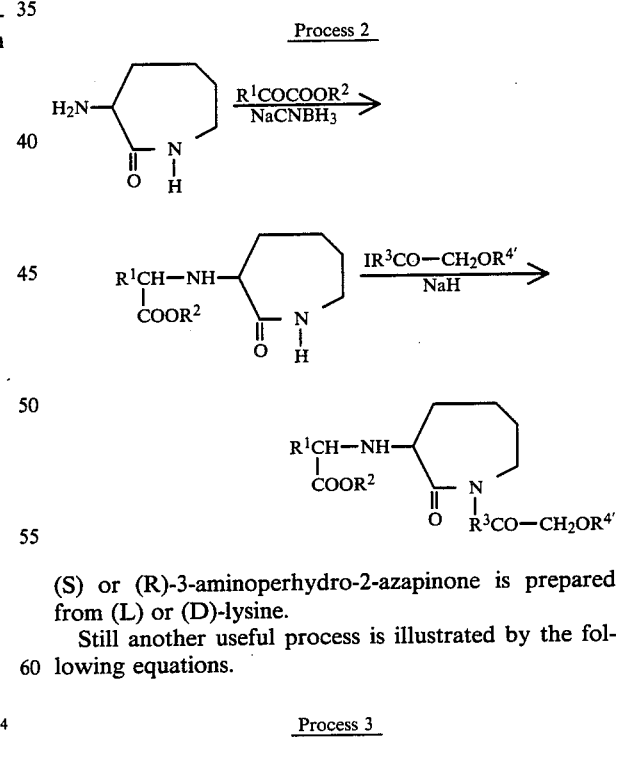

(S) or (R)-3-aminoperhydro-2-azapinone is prepared from (L) or (D)-lysine.

Still another useful process is illustrated by the following equations.

Process 3

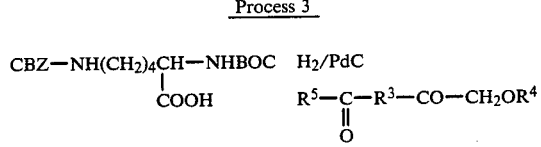

-continued
Process 3

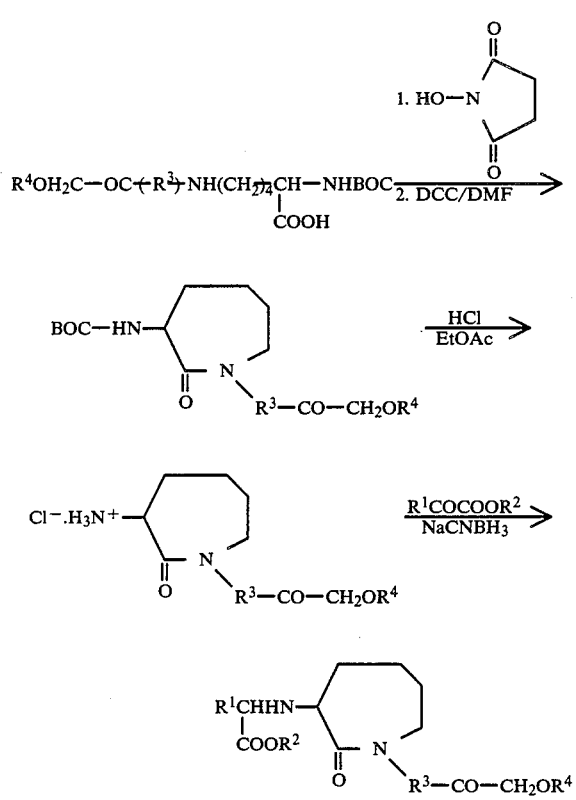

CBZ = benzyloxycarbonyl,
BOC = tertiarybutyloxycarbonyl,
DCC = dicyclohexylcarbodiimide
$R^5$ = H or loweralkyl An additional useful process is shown by the following equations:

Process 4

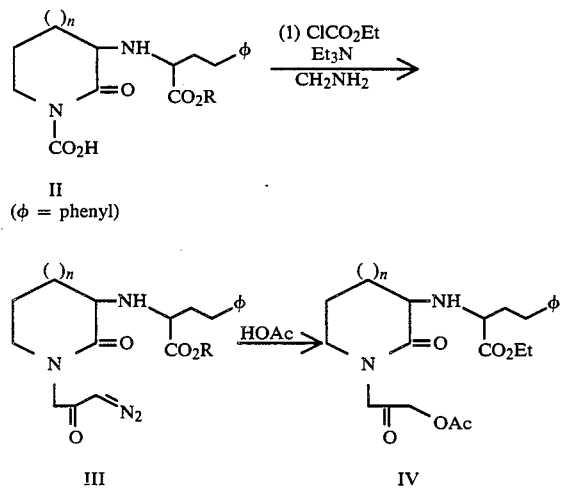

-continued
Process 4

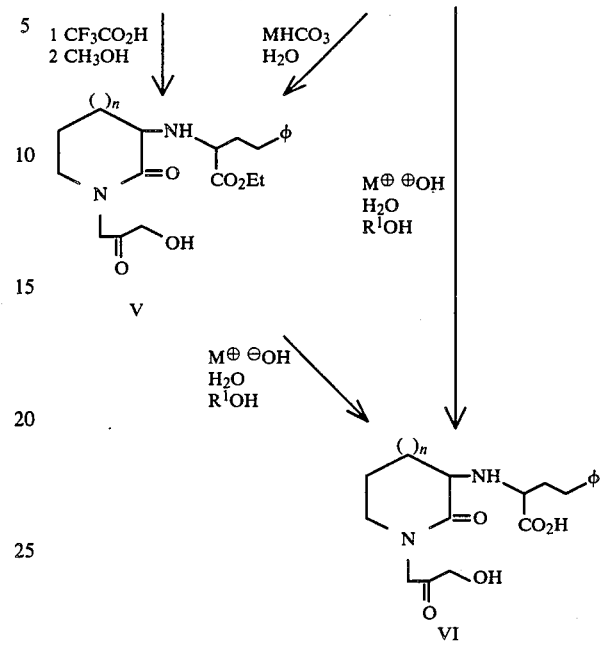

Lactam carboxylic acid II, ring size ranging from 6 to 8 (n = 1,2,3) prepared via synthetic sequences reported in European Patent Application No. 81106370.0, can be reacted with an alkoxyl halo formate such as ethyl chloro formate and a tertiary amine such as triethylamine in an aprotic solvent such as THF to give, upon filtration, the mixed anhydride intermediate which, on reaction with excess diazomethane in ether, gives diazoketone III. Reaction of diazoketone III in refluxing acetic acid produces acetate IV which, upon treatment with a metal hydroxide in water, affords hydroxymethyl ketone VI. Alternatively, reaction of diazoketone III in trifluoroacetic acid followed by hydrolysis of the trifluoro acetate with methanol or ethanol produces hydroxymethyl ketone ester V. Reaction of V with sodium hydroxide in water provides an alternative route to hydroxymethyl ketone acid VI.

Hydroxyketone ester V may be prepared from acetate IV by treatment of IV with potassium or sodium bicarbonate in $H_2O$.

The compounds of this invention inhibit angiotensin converting enzyme and thus block conversion of the decapeptide antiotensin I to angiotensin II. Angiotensin II is a potent pressor substance. Thus blood-pressure lowering results from inhibition of its biosynthesis especially in animals and humans whose hypertension is angiotensin II related. Furthermore, converting enzyme degrades the vasodepressor substance, bradykinin. Therefore, inhibitors of angiotensin converting enzyme may lower blood pressure also by potentiation of bradykinin. Although the relative importance of these and other possible mechanisms remains to be established, inhibitors of angiotensin converting enzyme are effective antihypertensive agents in a variety of animals models and are useful clinically, for example, in many human patients with reno-vascular, malignant and essential hypertension. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta*, 206, 136 (1970) in which the hydrolysis of carbobenzyloxyphenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.*, 125, 96 (1967).

Thus, the compounds of the invention are useful in treating hypertension. They are also of value in the management of acute and chronic congestive heart failure, in the treatment of secondary hyperaldosteronism, scleroderma, primary and secondary pulmonary hypertension, renal failure and renal vascular hypertension, and in the management of vascular disorders such as migraine. The application of the compounds of this invention for these and similar disorders will be apparent to those skilled in the art.

In the management of hypertension and those clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 10 to 200 mg. per patient per day which can be administered in single or multiple doses. Preferably, the dosage range will be about 20 to 100 mg. per patient per day.

It is often advantageous to administer compounds of this invention in combination with other antihypertensives and/or diuretics. For example, the compounds of this invention can be given in combination with such compounds as amiloride, atenolol, bendroflumethiazide, chlorothalidone, chlorothiazide, clonidine, cryptenamine acetate and cryptenamine tannates, deserpidine, diazoxide, guanethidene sulfate, hydralazine hydrochloride, hydrochlorothiazide, hydroflumethiazide, metolazone, metroprololtartate, methyclothiazide, methyldopa, methyldopate hydrochloride, minoxidil, (S)-1-{[2-(3,4-dimethoxyphenyl)ethyl]amino}-3-}[4-(2-thienyl)-1H-imidazol-2-yl]phenoxy}-2-propanol, polythiazide, the pivaloyloxyethyl ester of methyldopa, indacrinone and variable ratios of its enantiomers, nifedipine, verapamil, diltiazam, flumethiazide, bendroflumethiazide, atenolol, (+)-4-{3-{-[2-(1-hydroxycyclohexyl)ethyl]-4-oxo-2-thiazolidinyl}propyl}benzoic acid, bumetanide, prazosin, propranolol, rauwolfia serpentina, rescinnamine, reserpine, spironolactone, timolol, trichlormethiazide, benzthiazide, quinethazoke, tricrynafan, triamterene, acetazolamide, aminophylline, cyclothiazide, merethoxylline procaine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the antihypertensives of this invention effective clinically in the 20-100 milligrams per day range can be effectively combined at levels at the 4-100 milligrams per day range with the following compounds at the indicated per day dose range: hydrochlorothiazide (10-100 mg), timolol (5-60 mg), methyl dopa (65-2000 mg), the pivaloyloxyethyl ester of methyl dopa (30-1000 mg), indacrinone and cariable ratios of its enantiomers (25-150 mg) and +)-4-{3-{[2-(1:hydroxycyclohexyl)ethyl]-4-oxo-2-thiazolidinyl}propyl}-benzoic acid (10-100 mg).

In addition, the triple drug combinations of hydrochlorothiazide (10-100 mg) plus timolol (5-60 mg) plus converting enzyme inhibitor of this invention (4-100 mg) or hydrochlorothiazide (10-100 mg) plus amiloride (5-20 mg) plus converting enzyme inhibitor of this invention (4-100 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 4 to 100 mg of a compound or mixture of compound of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

The following examples illustrate preparation of representative compounds of the present invention. All temperatures are in degrees Celsius.

EXAMPLE 1

1-(3-Diazo-2-oxo-1-propyl)-3-(1-ethoxycarbonyl-3-phenyl-1-propyl)-aminoperhydro-2-azodinone A solutin of 3.4 g of 1-carboxymethyl-3-(1-ethoxycarbonyl-3-phenyl-1-propyl)-aminoperhydro-2-azodinone (+ isomer) in 70 ml of THF was cooled to $-15°$ C. and to it with vigorous stirring was added dropwise 0.86 ml of ethylchloroformate followed by 1.22 ml of triethylamine. After stirring for 10 minutes at $-15°$ C., the reacion mixture was filtered in a nitrogen atmosphere to remove triethylamine hydrochloride. To the THF solution was added a solution of diazomethane in ether [diazomethane was prepared from 2.9 g of N-nitrosomethylurea by a procedure reported in *Organic Syntheses Coll,* Vol I., pp 165]. The yellow reaction mixture was stirred 12 hours at 0° C. whereupon it was filtered and volatiles were evaporated at reduced pressure. The crude product was chromatographed (silica, ethyl acetate) to give 3.7 g of product. NMR (CDCl3, TMS) 1.3 (t, 3H); 1.4–2.2 (m, 10H); 2.7 (t, 2H); 3.2–4.6 (m, 9H); 4.2 (q, 2H); 5.5 (s, 1H); 7.2 (s, 5H). TLC (silica, ethyl acetate) $R_f=0.74$.

EXAMPLE 2

1-(3-Acetoxy-2-oxo-propyl)-3-(1-carboxy-3-phenyl-1-propyl)aminoperhydro-2-azocinone A solution of 1,395 g of diazoketone of Example 1 in 28 ml of acetic acid with 0.100 g of cuprous acetate was refluxed for 10 minutes whereupon the reaction mixture was cooled, filtered and the acetic acid removed at reduced pressure. The crude product was chromatographed (silica, 1:1 hexane: ethyl acetate) to produce 0.82 g of product.

TLC (silica, ethyl acetate) $R_f=0.078$.

NMR (CDCl3, TMS) 1.2 (t, 3H); 1.4–20 (m, 10H); 2.1 (s, 3H); 2.6 (It, 2H); 3.2 (t, 3H); 3.5–4.2 (m, 7H); 4.6 (s, 2H); 7.1 (s, 5H).

EXAMPLE 3

1-(3-Hydroxy-2-oxo-propyl)-3-(1-ethoxycarbonyl-3-phenyl-1-propyl)aminoperhydro-2-azocinone To a solution of 0.82 g of the acetate in 20 ml of methanol was added a solution of 0.75 g of potassium bicarbonate in 7.5 ml of water and the combined solution was refluxed for 10 minutes. Upon cooling, the reaction mixture was diluted with 15 ml of water and the methanol was removed at reduced pressure. The aqueous mixture was extracted with ethyl acetate (2×50 ml). The combined organic fractions were dried over MgSO4 and, after filtration, the ethyl acetate was removed at reduced pressure to give 0.72 g of product. TLC (silica, ethyl acetate) $R_f=0.34$. NMR (CDCL3, TMS) 1.3 (t, 3H); 1.4–2.0 (m, 10H), 2.4–2.8 (t, m, 4H); 3.2 (t, 2H); 3.4–3.9 (m, 2H); 4.2 (q, 2H), 4.1 (ABq, 2H); 4.3 (s, 2H); 7.1 (s, 5H).

EXAMPLE 4

1-(3-Hydroxy-2-oxo-propyl)-3-(1-carboxy-3-phenyl-1-propyl)aminoperhydroazocinone A solution of 0.120 g of the compound of Example 3 in 2.2 ml of a 1N sodium hydroxide solution was stirred overnight at room temperature. Whereupon it was made acidic (pH=5) with acetic acid and chromatographed (DOWEX 50-2x, H2O, and 5% Pyridine). Upon freeze drying of the resultant eluant, 95 mg of pure acid was isolated as a white solid.

TLC (silica, 85:85:15, ethanol:methylene chloride::ammonium hydroxide) $R_f=0.42$ NMR (DC3OD, TMS) 1.4–2.2 (m, 10H); 2.3–2.7 (t, 2H); 3.15 (t, 2H); 3.3–3.8 (m, 2H); 4.1–4.6 (m, 4H) 7.15 (s, 5H).

What is claimed is:

1. A compound having the formula:

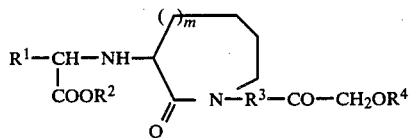

m is 1 to 3;

$R^1$ is $C_1$–$C_8$alkyl; substituted $C_1$–$C_5$alkyl wherein the substituent is amino, $C_1$–$C_8$-alkanoylamino, hydroxy, amino-$C_1$–$C_8$-alkylthio, amino-$C_1$–$C_8$-alkoxy, $C_6$–$C_{12}$-arylthio, $C_6$–$C_{12}$aryloxy or $C_6$–$C_{12}$-arylamino; substituted or unsubstituted $C_6$–$C_{12}$ arylalkyl wherein the alkyl portion has 1 to 3 carbon atoms optionally substituted with amino, hydroxy or $C_1$–$C_8$alkanoylamino, $R^2$ is hydrogen; $C_1$–$C_8$alkyl; $C_6$–$C_{12}$aryl-$C_1$–$C_8$-alkyl;

$R^3$ is $(CH_2)_q$ where q is 1 or 2; and, $R^4$ is hydrogen.

2. A compound having the formula:

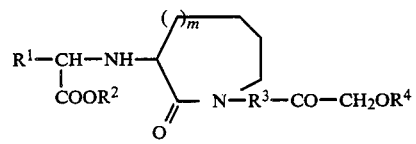

wherein m is 1 or 2;

$R^1$ is $C_1$–$C_8$alkyl; substituted $C_1$–$C_5$alkyl wherein the substituent is amino, $C_1$–$C_8$ alkanoylamino, hydroxy, amino-$C_1$–$C_8$-alkylthio, $C_6$–$C_{12}$arylthio, $C_6$–$C_{12}$-aryloxy; substituted or unsubstituted $C_6$–$C_{12}$ wherein the alkyl portion has 1–3 carbon atoms optionally substituted with amino, hydroxy or $C_1$–$C_8$alkanoylamino;

$R^2$ is hydrogen; $C_1$–$C_8$alkyl; $C_6$–$C_{12}$aryl-$C_1$–$C_8$-alkyl;

$R^3$ is $(CH_2)_q$ where q is 1 or 2;

$R^4$ is hydrogen and, the pharmaceutically acceptable salts thereof.

3. A compound having the formula:

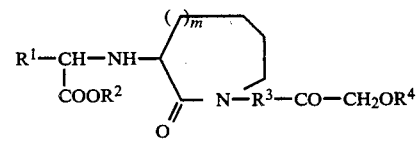

m is 1 or 2;

$R^1$ is $C_1$–$C_8$alkyl; substituted $C_1$–$C_5$alkyl wherein the substituent is amino, $C_1$–$C_8$-alkanoyl amino, hydroxy, $C_6$–$C_{12}$arylthio, $C_6$–$C_{12}$aryloxy; substituted or unsubstituted $C_6$–$C_{12}$ wherein the alkyl groups have 1-3 carbons;

$R_2$ is hydrogen; loweralkyl; benzyl;

$R^3$ is $(CH_2)_q$ where q is 1 or 2;

$R^4$ is hydrogen and, the pharmaceutically acceptable salts thereof.

4. A pharmaceutical composition useful for treating hypertension comprising a pharmaceutically acceptable carrier; and, an antihypertensively effective amount of a compound of claim 1.

5. The composition of claim 4 which includes another antihypertensive and/or diuretic selected from the group consisting of amiloride, atenolol, bendroflumethiazide, chlorothalidone, chlorothiazide, clonidine, cryptenamine acetate and cryptenamine tannates, deserpidine, diazoxide, guanethidene sulfate, hydralazine hydrochloride, hydrochlorothiazide, hydroflumethiazide, metolazone, metroprololtartate, methylclothiazide, methyldopa, methyldopate hydrochloride, minoxidil, (S)-1-{[2-(3,4-dimethoxyphenyl)ethyl]amino}-3-{[4-(2-thienyl)-1H-imidazol-2-yl]phenoxy}-2-propanol, polythiazide, the pivaloyloxyethyl ester of methyldopa, indacrinone and variable ratios of its enantiomers, nifedipine, verapamil, diltiazam, flumethiazide, bendroflumethiazide, atenolol, ($\pm$)-4-{3-{-[2-(1-hydroxycyclohexyl)ethyl]-4-oxo-2-thiazolidinyl}propyl}benzoic acid, bumetanide, prazosin, propanolol, rauwolfia serpentina, rescinnamine, reserpine, spironolactone, timolol, trichlormethiazide, benzthiazide, quinethazone, tricrynafan, triamterene, acetazolamide, aminophylline, cyclothiazide, merethoxylline procaine, as well as admixtures and combinations thereof.

6. A method of treating hypertension which comprises administering to a patient in need of such treatment an antihypertensively effective amount of a compound of claim 1.

* * * * *